United States Patent [19]

Lucki et al.

[11] 4,207,208

[45] Jun. 10, 1980

[54] METHOD FOR REGENERATION AND ACTIVITY IMPROVEMENT OF SYNGAS CONVERSION CATALYST

[75] Inventors: Stanley J. Lucki, Runnemede; James A. Brennan, Cherry Hill, both of N.J.

[73] Assignee: Mobil Oil Corporation, New York, N.Y.

[21] Appl. No.: 970,590

[22] Filed: Dec. 18, 1978

[51] Int. Cl.² ............... B01J 29/06; B01D 15/06
[52] U.S. Cl. .................... 252/455 Z; 252/419; 260/449.6 R
[58] Field of Search .............. 252/416, 419, 455 Z; 260/449.6 R

[56] References Cited

U.S. PATENT DOCUMENTS

| | | | |
|---|---|---|---|
| 2,728,786 | 12/1955 | McGrath et al. | 260/449.6 |
| 2,786,817 | 3/1957 | Rottig et al. | 260/449.6 X |
| 3,684,738 | 8/1972 | Chen | 252/416 X |
| 4,086,262 | 4/1978 | Chang et al. | 260/449.6 R |

*Primary Examiner*—Carl F. Dees
*Attorney, Agent, or Firm*—Charles A. Huggett; Raymond W. Barclay

[57] ABSTRACT

A method is disclosed for the treatment of single particle iron-containing syngas (synthes.s gas) conversion catalysts comprising iron, a crystalline acidic aluminosilicate zeolite having a silica to alumina ratio of at least 12, a pore size greater than about 5 Angstrom units and a constraint index of about 1–12 and a matrix. The catalyst does not contain promoters and the treatment is applicable to either the regeneration of said spent single particle iron-containing catalyst or for the initial activation of fresh catalyst. The treatment involves air oxidation, hydrogen reduction, followed by a second air oxidation and contact of the iron-containing single particle catalyst with syngas prior to its use for the catalytic conversion of said syngas. The single particle iron-containing catalysts are prepared from a water insoluble organic iron compound.

16 Claims, No Drawings

METHOD FOR REGENERATION AND ACTIVITY IMPROVEMENT OF SYNGAS CONVERSION CATALYST

The Government of the United States of America has rights in this invention pursuant to Contract No. E(49-18)2276 awarded by the U.S. Energy Research and Development Administration.

CROSS REFERENCE TO RELATED CASES

This application is related to application Ser. No. 970,307 filed Dec. 18, 1978 entitled "Conversion of Synthesis Gas with Iron-Containing Catalyst" which describes and claims the catalyst with which the instant application is concerned, as well as the conversion of syngas over said catalyst.

BACKGROUND OF THE INVENTION

Field of the Invention

This invention is concerned generally with processes for converting synthesis gas, i.e. mixtures of gaseous carbon oxides with hydrogen or hydrogen donors, to hydrocarbon mixtures and more specifically, with catalyst treatment.

Processes for the conversion of coal and other hydrocarbons, such as natural gas, to a gaseous mixture consisting essentially of hydrogen and carbon monoxide and/or dioxide are well known. Those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels is given in Encyclopedia of Chemical Technology, Edited by Kirk-Othmer, Second Edition, Volume 10, pages 353–433 (1966), Interscience Publishers, New York, New York.

It is also well known that synthesis gas will undergo conversion to reduction products of carbon monoxide, such as hydrocarbons, at from about 300° F. to about 850° F., under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. Catalysts that have been studied for this and related processes include those based on iron, cobalt, nickel, ruthenium, thorium, rhodium and osmium, or their oxides.

Recently, it has been discovered that the conversion of synthesis gas into valuable products can be greatly enhanced by employing a special type of crystalline alumino-silicate zeolite exemplified by ZSM-5 in admixture with a conventional Fischer-Tropsch catalyst. Thus, for example, in U.S. Pat. No. 4,086,262, there is disclosed a process for the conversion of syngas by passing the same at elevated temperature over a catalyst which comprises an intimate mixture of a Fischer-Tropsch component and a special type of zeolite such as ZSM-5. Said patent points out that the products produced are hydrocarbon mixtures which are useful in the manufacture of heating oil, high octane gasoline, aromatic compounds, and chemical intermediates.

Although U.S. Pat. No. 4,086,262 is primarily directed to multi-particle composite catalysts, i.e., the crystalline aluminosilicate component (one particle) is physically admixed with the Fischer-Tropsch component (another particle), nevertheless, Example 5 of said patent does disclose a single particle iron-containing catalyst in an alumina matrix.

As can well be appreciated, the patent and technical literature relating to the Fischer-Tropsch process, is, indeed, extensive and the various catalysts reported in the prior art have been used by themselves as well as in admixture with catalytically inactive supports such as kieselguhr. Although the reasons for using catalytically inactive supports have varied, nevertheless, it would appear that one reason for using the same was that it resulted in increased surface area of the Fischer-Tropsch component upon which it was deposited or admixed and that it also aided in controlling the heat requirements of the overall exothermic reactions.

It is also known in the art to admix a Fischer-Tropsch component with a material, such as silica-alumina which is known to be catalytically active for the conversion of hydrocarbons.

Copending application Ser. No. 970,307, filed Dec. 18, 1978 (the entire disclosure of which is incorporated by reference) is directed towards the use of a water-insoluble iron derivative of an organic compound such as iron oxalate to prepare single particle catalysts and the discovery that such catalysts are far more effect for the conversion of syngas than the corresponding catalysts made from water-soluble iron salts.

DESCRIPTION OF PREFERRED EMBODIMENTS

The novel process of this invention is directed towards the treatment of the single particle iron-containing catalysts of aforementioned Ser. No. 970,307, filed Dec. 18, 1978. The novel treatment of this invention is applicable either to enhance the activity of the fresh iron-containing catalysts or to restore the activity of said catalysts which had become deactivated during use in the conversion of syngas.

The novel process of this invention involves carrying out four steps in sequence which can be defined as first oxidizing either the fresh or spent catalyst in a stream of flowing air at a pressure in the range of about 0–200 psig for 0.1 to 16 hours at temperatures between 500° and 1,000° F. The second step resides in reducing the treated catalyst in a stream of flowing hydrogen at pressures in the range of 0–200 psig for 0.1 to 16 hours at temperatures between 500° and 1,000° F. The third step involves reoxidizing said previously reduced catalyst by contacting the same in a stream of air at pressures in the range of from 0–200 psig for 0.1 to 16 hours at temperatures between 500° and 1,000° F. The fourth step in the novel treatment process of this invention involves activation of the catalyst by treatment of the same with syngas at atmospheric pressure and at temperatures of about 550°–650° F. for periods of time ranging from about ½ hour up to about 24 hours.

It is pointed out however, that the first step of air oxidation can be omitted in the regeneration of spent catalyst which is not highly coked, i.e. it has only been used in short cycles. The first step is always necessary for the activation of fresh catalyst.

It is recognized that it is notoriously old in the Fischer-Tropsch art to reactivate spent catalysts by a wide variety of techniques which include not only oxidation, but also reduction. One representative patent in this area is U.S. Pat. No. 2,273,864 which discloses a method for reactivating catalysts comprising subjecting the catalyst to at least one sequence of oxidizing and reducing steps above 700° F. and thereafter subjecting the catalyst to at least one sequence of oxidizing and reducing steps below 700° F. It is to be noted however, that the novel process of this invention contains very critical steps which must be performed in the sequence previously mentioned. Additionally, the novel process of this invention is applicable to a specific type of Fischer-Tropsch catalyst which had been prepared utilizing a water insoluble organic iron compound. For reasons which are not completely understood, it has been found that it is absolutely necessary when utilizing catalysts of this type to have the aforementioned pretreatment with syngas immediately prior to the use of these catalysts for the processing of said syngas. In other words, although one of the steps in the novel process of this invention involves treatment of the catalyst with hydrogen, it is absolutely critical that this hydrogen treatment step not be the last step prior to use of the catalyst in syngas conversion. The vast majority of prior art reactivation processes, no matter what the particular sequence, generally uses as a last step therein treatment of the catalyst with hydrogen immediately prior to its use for the conversion of syngas. Although this technique may very well be effective in treatment of iron-containing Fischer-Tropsch catalysts prepared by conventional techniques, nevertheless, it is totally inapplicable to the single particle Fischer-Tropsch catalyst prepared from water insoluble organic compounds which are utilized in the process of this invention.

The regeneration process of this invention results in the restoration of activity of the spent catalyst to an unusually high degree and enables the catalyst to be regenerated many times without any significant adverse effects.

The novel process of this invention is concerned with contacting synthesis gas with either a fixed bed or fluid catalyst which comprises at least three separate components which are present in a single particle as opposed to a mixture of three separate particles. The catalyst with which this invention is concerned comprises iron, an acidic crystalline aluminosilicate zeolite having a pore size of about 5 Angstrom units, a silica alumina ratio of at least 12, and a constraint index of about 1–12 (preferably ZSM-5) and a siliceous matrix material. The crystalline aluminosilicates employed are fully set forth in aforementioned U.S. Pat. No. 4,086,262 which is herein incorporated by reference. The preferred class of zeolites used is exemplified by ZSM-5, ZSM-11, ZSM-12, etc. As has heretofore been stated, the manner in which the iron is introduced into the catalyst is of prime importance.

The matrix portion of the single particle fluid catalyst is not narrowly critical and suitable matrices include silica, alumina, silica-alumina, silica-zirconia, silica-magnesia, etc.

One surprising feature of the instant catalysts is that they are unpromoted and yet they still exhibit high activity with little or no evident aging, and, in fact, are capable of converting syngas to a naphtha product while producing no more than 30 weight percent of methane plus ethane, based on total hydrocarbons. In fact, the use of promoters, which the prior art found necessary in previous iron-containing catalysts, is definitely not preferred due to the fact that most promoters are alkaline in nature and they have a tendency to migrate to the acidic crystalline aluminosilicate zeolite component and to decrease the activity of the same.

Therefore, it would appear that the single particle catalyst of the instant invention represents a significant departure from the teachings of the prior art in that not only are alkaline promoters not necessary for sustained operation but, in fact, are detrimental to the activity of the zeolitic component.

The single particle iron-containing catalyst can be prepared by adding the appropriate acidic crystalline aluminosilicate previously defined and a water insoluble iron derivative of an organic iron to a hydrogel before drying, homogenizing the same, and thereafter forming either fixed bed or fluid catalysts by conventional techniques.

The water-insoluble derivatives of organic compounds include water-insoluble organic iron salts such as the oxalate, the formate, as well as mixtures thereof.

The amount of water-insoluble iron derivative of an organic compound which is added is not narrowly critical and an amount sufficient to produce 2.5 to 20 weight percent and more preferably 2.5 to 10 weight percent based on the finished catalyst is used.

One embodiment for catalyst preparation resides in the in situ formation of the water insoluble organic iron derivative in the hydrogel, In this embodiment a water soluble iron salt such as iron sulfate is added to the hydrogel followed by treatment with oxalic, formic or gluconic acid in order to form the organic salt in situ.

Following the addition of the water insoluble organic iron salt, (either directly or prepared in situ), the catalyst can be formulated into a fixed bed catalyst or, preferably, into a fluid catalyst by conventional techniques.

It is to be understood that methods of making fluidized catalysts containing crystalline aluminosilicate zeolites and siliceous matrices are well known in the art. Thus, for example, a composite of the crystalline alumino-silicate zeolite and a siliceous matrix can be made by admixing an aqueous alkali metal silicate with or without a particulate weighting agent, such as kaolin clay, desirably as a dispersion in water so as to intimately mix the clay particles with the alkali metal silicate. This admixing is conveniently done at room temperature, although, of course, higher or lower temperatures may be employed if desired. The mixture is then heated, generally to a temperature of from 100°–160° F. and acid is added to adjust the pH to from about 8–10. The temperature is maintained for a time of about 1–6 hours or longer. At this point, if a silica-zirconia weighting agent (e.g. clay) matrix is desired, a zirconium salt is added, desirably as an aqueous solution thereof. Acid is then added to reduce the pH to about 4–7 and form a silica gel weighting agent or a silica gel-zirconia gel weighting agent slurry, which is then admixed with a slurry of the acidic crystalline aluminosilicate zeolite and the water insoluble organic iron salt previously described. The resulting composite is then homogenized and then treated with a source of ammonium ions or hydrogen ions in order to reduce the sodium content to a low level which is desirably less than about 0.1% sodium and then spray dried to produce fluid size particles.

As is generally known in fluid catalysts for catalytic cracking, the catalyst additionally includes a weighting agent. The most preferred weighting agent is kaolin clay. Other weighting agents may be substituted in whole or in part for the kaolin clay so long as the weighting agents are not detrimental to the finished catalyst.

The relative proportion of crystalline aluminosilicate zeolite to matrix is not narrowly critical and it can range from about 5–40 weight percent of the matrix.

As has been indicated earlier, the crystalline aluminosilicate zeolite, the iron component and the matrix are then thoroughly mixed in a form of an aqueous slurry in order to homogenize the same and thereafter subdivided and dried to form the desired particles. A particularly good method of making microspherical particles (e.g. of particle size of about 1–200 microns) especially suitable for use in the fluidized process of this invention is spray-drying, preferably under high pressure, e.g., of the order of about 200–2,000 psig and preferably from about 1,000–1,500 psig.

The spray-drying temperature is ordinarily within the range of 200°–1,000° F. The temperature used will depend on such factors as the quantity of material to be dried and the quantity of air used in the drying. The evaporation rate will vary depending on the quantity of air used in the drying. The temperature of the particles which are being dried is preferably within the range of 150°–300° F. at the completion of the drying.

The drying is preferably affected by a process in which the particles to be dried and a hot air stream are moving in the same direction for the entire drying period (concurrent drying) or where the hot stream flows in the opposite direction (countercurrent drying), or by semi-concurrent drying. It is to be understood that spray-drying to form fluidized catalysts is well known in the art and a representative procedure is described in U.S. Pat. No. 3,553,104, the entire contents of which are incorporated by reference.

The iron-containing catalysts are thereafter heated in order to decompose the organic iron compound. The temperature utilized is not critical and it can range from 115° F. to 1200° F. for periods of time ranging from about 1 to 48 hours.

Another embodiment for catalyst preparation resides in a modification involving the in situ formation of the water insoluble organic iron salt. In this embodiment, a water-soluble iron salt such as ferrous sulfate or iron gluconate is added to an alumina dispersion followed by addition of an appropriate organic acid such as oxalic acid in order to form an alumina-iron oxalate composition. This composition can be used as the source of iron by the addition of the same to the hydrogel-containing matrix and crystalline aluminosilicate zeolite followed by processing in the manner previously described.

A particularly desirable embodiment resides in the use of matrices made from mixtures of colloidal silica and colloidal alumina instead of conventional procedures in which sodium silicate and aluminum sulfate are employed. In this embodiment colloidal alumina is added to colloidal silica which usually contains a slurry of a weighting agent such as clay. Crystalline aluminosilicate zeolite and water-insoluble organic iron salt are added followed by homogenizing and spray-drying in the manner previously described.

The acidic crystalline aluminosilicate component of the catalyst is characterized by a pore dimension greater than about 5 Angstroms, i.e., it is capable of sorbing paraffins, and it has a silica-to-alumina ratio of at least 12 and a constraint index within the range of 1 to 12. Zeolite A, for example, with a silica-to-alumina ratio of 2.0 is not useful in this invention, and it has no pore dimension greater than about 5 Angstroms.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

The acidic crystalline aluminosilicate component preferably is in the hydrogen form.

The catalysts referred to herein utilize members of a special class of zeolites exhibiting some unusual properties. They are very active even with silica-to-alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention comprise, in combination: a silica-to-alumina ratio of at least about 12; and a structure providing constrained access to the crystalline free space.

The silica-to-alumina ratio referred to may be determined by conventional analysis. This ratio is meant to represent as closely as possible, the ratio in the rigid anionic framework of the zeolite crystal and to exclude aluminum in the binder or in cationic or other form within the channels. Although zeolites with a silica-to-alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic characteristic is advantageous in the present invention.

The zeolites useful as catalysts in this invention freely sorb normal hexane and have a pore dimension greater than about 5 Angstroms. In addition, there structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of 12-membered rings do not generally appear to offer sufficient constraint to produce the advantageous conversions desired in the instant invention, although structures can be conceived, due to pore blockage or other causes, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1,000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e. 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
| --- | --- |
| Erionite | 38 |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |
| Beta | 0.6 |
| ZSM-4 | 0.5 |
| Acid Mordenite | 0.5 |
| REY | 0.4 |
| Amorphous silica-alumina | 0.6 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint index seems to very somewhat with severity of operation (conversion). Therefore, it will be appreciated that it may be possible to so select test conditions to establish multiple constraint indexes for a particular given zeolite which may be both inside and outside the above-defined range of 1 to 12.

Thus, it should be understood that the parameter and property "Constraint Index" as such value is used herein as an inclusive rather than exclusive value. That is, a zeolite when tested by any combination of conditions within the testing definition set forth hereinabove to have a constraint index of 1 to 12 is intended to be included in the instant catalyst definition regardless that the same indentical zeolite, tested under other defined conditions may give a constraint index value outside of 1 to 12.

The class of zeolites defined herein is exemplified by ZSM-5, ZSM-11, ZSM-12, ZSM-35, and ZSM-38, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-35 is described in U.S. Pat. No. 4,016,245 and ZSM-38 is described in U.S. Pat. No. 4,046,859, both of which are incorporated herein by reference.

Conversion of syngas is carried out at temperatures ranging from about 500°–600° F. and more preferably from 550° to about 580° F. The novel process of this invention is carried out at gas hourly space velocities (GHSV), ranging from 400 to 20,000 and more desirably from 500 to 6,000, based on fresh feed and total catalyst volume. Hydrogen to carbon oxides ratios can vary from 0.5:1 to 2:1 and more preferably are about 1:1, pressures ranging from 50 to 1,000 psig and more preferably from 150 to 400 psig are employed.

It is to be understood that although this invention has been described with reference to iron only, the catalyst can contain minor amounts of additional substances such as tin, phosphorus and tungsten, rare earth, vanadium, manganese, molybdenum, etc.

The following examples will illustrate the novel process of this invention.

EXAMPLE 1

A fluid catalyst matrix was prepared by adding 10,722 grams Q-Brand sodium silicate to a slurry of 930 grams kaolin clay in 112.5 lbs $H_2O$. After heating to 120° F., 1012 grams of 97% $H_2SO_4$ was added. At pH 10.51 the gel was heated to 140° F. for two hours and a solution of 186.6 grams aluminum sulfate in 746 cc $H_2O$ was added, followed by 166.7 grams of sodium zirconium silicate in 1617 cc $H_2O$. The pH was adjusted to 4.58 by addition of $H_2SO_4$ and left to stand overnight.

EXAMPLE 2

The catalyst of this example was prepared by filtering one-half of the gel matrix prepared in Example 1. The filter cake was slurried with 300 grams $(NH_4)_2SO_4$ in 6 liters of water, filtered again, and washed with water until the washings were free of sulfate. The gel was homogenized with the addition of 1132 grams of low sodium ZSM-5 zeolite (30.6% solid content) in 3400 cc $H_2O$ and 1204 grams ferrous oxalate dihydrate, and the mixture spray dried. An air calcination for 3 hours at 1000° F. gave the finished catalyst which contained 9.9% iron. Other properties are listed below:

PROPERTIES OF IRON/ZSM-5 FLUID SYN GAS CATALYSTS

| Composition, Wt. % | |
|---|---|
| SiO$_2$ | 73.8 |
| Al$_2$O$_3$ | 6.1 |
| Fe$_2$O$_3$ (Fe) | 14.2 (9.9) |
| ZnO$_2$ | ~1.5 |
| HZSM-5 | ~30 |

| Composition, Wt. % | |
|---|---|
| SiO$_2$/Al$_2$O$_3$ (zeolite) | 70/1 |
| Surface Area, m$^2$/g | 287 |
| Particle Density, g/cc | .575 |
| Real Density, g/cc | 2.65 |
| Packed Density, g/cc | 0.35 |
| Pore Volume, cc/g | 0.91 |

PARTICLE SIZE DISTRIBUTION

| Microns | Calculated Wt % |
|---|---|
| 0-20 | 2.2 |
| 0-30 | 4.3 |
| 0-40 | 9.1 |
| 0-60 | 28.8 |
| 0-80 | 56.4 |
| 0-100 | 79.3 |
| Mean Diameter | 75.6 |
| Attrition Index (0-20) | 21.7 |

EXAMPLE 3

The mixed silica-alumina sol catalyst was prepared by adding 2000 grams Ludox-LS ® silica sol in 1535 cc of water to a clay dispersion containing 348.8 grams WP kaolin in 4677 cc H$_2$O. An alumina dispersion prepared by the addition of 666.7 grams Dispal-M ® alumina to 40 grams of 70% nitric acid+6040 cc water was then added to the above-prepared silica-clay mixture, followed by 3268 grams of the low sodium form of ZSM-5 in 2488 cc H$_2$O. Finally, a slurry containing 1049 grams ferrous oxalate dihydrate in 2489 cc H$_2$O was added and the mixture was then homogenized and spray-dried. The fluid catalyst was heated in nitrogen at ca. 1100° F. for three hours followed by a final air calcination for three hours at 1000° F. The finished catalyst contained 9.1% iron. Other properties are listed below:

Table

| Composition, wt % | |
|---|---|
| SiO$_2$ | 21 |
| Al$_2$O$_3$ | 21 |
| Clay | 11 |
| HZSM-5 | 34 |
| Fe$_2$O$_3$ | 13 |
| Real density, g/cc | 2.72 |
| Packed density, g/cc | 0.50 |
| Pore volume, cc/g | 0.48 |
| Zeolite/iron wt ratio | 3.8 |
| Particle size, microns | Wt % |
| 0-20 | 0.6 |
| 0-30 | 9.6 |
| 0-40 | 28.2 |
| 0-60 | 61.1 |
| 0-80 | 78.1 |
| 0-100 | 86.2 |
| Mean particle diameter | 53.0 microns |

Examples 4-7 will illustrate the novel process of this invention will regard to catalyst activation as well as comparisons with other methods of catalyst activation in connection with the syngas conversion.

In all cases, the catalyst of Example 2 was used and syngas (1:1 H$_2$/CO) was converted at 575° F., 200 psig and 575 GHSV.

The specific activation treatments as well as the results obtained in syngas conversion are shown in the table below.

Table

| Example | 4 | 5 | 6 | 7 |
|---|---|---|---|---|
| Stream Days | 0.9 | 0.9 | 1.8 | 1.9 |
| Treatment, 16Hr | 0 psig H$_2$-950° F. | 200 psig H$_2$-950° F. | 0 psig H$_2$/CO-610° F. | Air-950° F— 0 psig + H$_2$/CO-610° F. |
| CO Conversion, % | <1 | <1 | <1 | 78 (64) |
| H$_2$ Conversion, % | <1 | <1 | <1 | 65 (59) |
| Selectivity, % | | | | |
| C$_1$ + C$_2$ | — | — | — | 31 (29) |
| C$_5$+ | — | — | — | 50 (54) |

() indicates fresh catalyst data using standard activation with H$_2$/CO at 610° F. as disclosd in copending application Serial Number 970,307 filed December 18, 1978

It is observed that hydrogen treatment either at zero or 200 psig completely deactivates the catalyst. Further the standard activation procedure of H$_2$/CO synthesis gas at 610° F., failed to activate the catalyst after exposure to hydrogen. However, an oxygen treatment (initial temperature 750° F. in 10% air, final conditions 16 hr-100% air-950° F.) of this deactivated catalyst followed by the standard activation in synthesis gas yielded an active catalyst. Comparisons with fresh catalyst show a 14% higher CO conversion (78 vs 64).

EXAMPLE 8

The fixed bed version of the catalyst of Example 2 was evaluated for the conversion of syngas (1:1 H$_2$/CO) at 575° F., 200 psig, and 575 GHSV. The fresh air calcined catalyst was activated by treatment with 1:1 H$_2$/CO for 16 hours at 610° F. and 0 psig. The results calcined during 5 cycles as presented. Regeneration after cycles 1-3 was accomplished by treatment with air for 16 hours at 950° F. and 0 psig. Regeneration after cycle 4 was accomplished in accordance with the instant invention and was as follows:

(1) air for 16 hours at 950° F., 0 psig
(2) Hydrogen for 16 hours at 750° F., 0 psig
(3) Air for 16 hours at 950° F., 0 psig (4) H$_2$/CO for 16 hours at 610° F., 0 psig The results are shown in the following table.

TABLE

| REGENERATION OF CATALYST | | | | | |
|---|---|---|---|---|---|
| Cycle | 1 Fresh | 2 | 3 | 4 | 5 |
| Days on Stream | 1.9  5.9 | 1.9  5.9 | 1.9  5.9 | 1.9  5.9 | 1.9  5.8 |
| % Conversion | | | | | |
| CO | 64  64 | 65  65 | 59  57 | 51  49 | 68  71 |
| H$_2$ | 59  58 | 61  62 | 60  59 | 53  58 | 62  63 |
| % HC Selectivity | | | | | |
| C$_1$ + C$_2$ | 29  34 | 33  37 | 32  35 | 31  37 | 36  38 |
| C$_5$+ | 54  59 | 59  58 | 52  49 | 52  45 | 45  44 |
| % C$_5$ = in C$_5$ Fraction | 13  39 | 12  30 | 13  30 | 14  24 | 15  21 |

TABLE-continued

REGENERATION OF CATALYST

| Cycle | 1 Fresh | | 2 | | 3 | | 4 | | 5 |
|---|---|---|---|---|---|---|---|---|---|
| % MeC$_4$ = in C$_5$= | 87 | 82 | 80 | 80 | 79 | 78 | 79 | 76 | 80 | 78 |
| C$_6$ + Aromatics | 43 | 21 | 41 | 26 | 44 | 26 | 43 | 35 | 45 | 40 |

As can be seen, the activity for CO conversion dropped from 64 wt.% to 49% at the end of cycle 4 when only air regeneration was used. However, the regeneration procedure of this invention after cycle 4 resulted in even higher activity than the fresh catalyst 71% versus 64%.

EXAMPLE 9

The fixed bed version of the catalyst of Example 3 was evaluated for syngas conversion using different regeneration techniques. The test conditions as well as the results obtained are shown in the following table.

Aging and Regeneration of Catalyst
(Processing H$_2$/CO at 575° F., 200 psig and 1000 GHSV)

| Cycle | Fresh | 2$^{(a)}$ | | 3$^{(a)}$ | | 4$^{(b)}$ | | 5$^{(c)}$ |
|---|---|---|---|---|---|---|---|---|
| Stream Days | 1.9 | 5.9 | 1.9 | 5.9 | 1.9 | 3.9 | 1.8 | 5.8 | 0.9 |
| CO Conversion, % wt | 90 | 89 | 91 | 90 | 74 | 65 | 93 | 93 | 88 |
| H$_2$Conversion, % wt | 70 | 70 | 70 | 71 | 65 | 61 | 69 | 73 | 68 |
| HC Selectivity, % wt | | | | | | | | | |
| C$_1$ + C$_2$ | 38 | 37 | 40 | 43 | 42 | 41 | 43 | 44 | 44 |
| C$_5$ + | 44 | 47 | 42 | 39 | 39 | 40 | 38 | 37 | 36 |
| Olefins in C$_5$ Fraction, % wt | 15 | 23 | 11 | 17 | 18 | 22 | 16 | 21 | 16 |
| Aromatics in C$_6$ +, % wt | 41 | 25 | 31 | 26 | 31 | 26 | 38 | 30 | 41 |

$^{(a)}$Regeneration: 2 Hrs, 2% O$_2$, 750° F., 0 psig.
$^{(b)}$(16 Hr, H$_2$, 750° F., 0 psig) + (16 Hr, Air, 950° F., 0 psig) + (16 Hr, H$_2$/CO, 610° F., 0 psig)
$^{(c)}$(16 Hr, H$_2$, 750° F., 0 psig) + $\begin{pmatrix} \text{1 Hr, 10\% Air, 750° F., 0 psig} \\ \text{4 Hr, 100\% Air, 850° F., 0 psig} \end{pmatrix}$ + (16 Hr, H$_2$/CO, 600° F., 0 psig)

Following the third cycle the catalyst was subjected to a procedure similar to that used in the reactivation of catalyst in Example 8 where the sequence was one of air oxidation-hydrogen reduction-air oxidation. In this current procedure the initial oxidation was eliminated and the coked catalyst was treated in flowing hydrogen for 16 hours at 750° F. The air regeneration for 16 hours at 950° F. was followed by the standard activation in synthesis gas, H$_2$/CO, at 610° F. Comparisons with fresh and regenerated catalyst at 1.8 and 5.8 days on stream indicate that the activity for carbon monoxide conversion was completely restored using this procedure. The C$_1$ and C$_2$ yields, however, increased slightly while C$_5$+ yields decreased. Also of interest is the conclusion that a coked catalyst need not be air regenerated prior to the reduction step.

After catalyst reactivation total process time was 10.8 days. At this point an initial step was taken toward optimizing the regeneration procedure. Time (16 hrs) and temperature (750° F.) of hydrogen treatment of the used catalyst remained the same; however, air regeneration was conducted for one hour in 10% air at 750° F. followed by four additional hours in 100% air at 850° F. As is evidenced by the data the milder regeneration conditions employed were successful in reactivating the catalyst.

What is claimed is:

1. A method for treating either a fresh or spent single particle iron-containing syngas conversion catalyst composition prepared by forming a mixture of a water insoluble iron derivative of an organic compound, a matrix and an acidic crystalline aluminosilicate zeolite having a silica-to-alumina ratio of at least 12, a pore size greater than about 5 Angstrom units and a constraint index of about 1 to 12 which comprises:
   (a) oxidizing said catalyst in a stream of flowing air at a pressure in the range of 0–200 psig for about 0.1 to 16 hours at a temperature within the range of about 500°–1,000° F.,
   (b) treating the product from step (a) in a stream of flowing hydrogen at a pressure in the range of 0–200 psig for about 0.1 to 16 hours at a temperature within the range of about 500°–1,000° F.,
   (c) treating the product from step (b) in air at a pressure in the range of 0–200 psig for about 0.1–16 hours at a temperature within the range of about 500°–1,000° F., and
   (d) treating the product from step (c) with synthesis gas at atmospheric pressure at temperatures of about 550°–650° F. for about 0.5 to 24 hours.
2. The process of claim 1 wherein the catalyst has been spray-dried to produce fluid size particles.
3. The process of claim 1 wherein said water insoluble compound is ferrous oxalate.
4. The process of claim 2 wherein said water insoluble compound is ferrous oxalate.
5. The process of claim 4 wherein said water insoluble iron oxalate is formed in situ.
6. The process of claim 1 wherein said matrix is a siliceous matrix.
7. The process of claim 1 wherein said matrix comprises alumina.
8. The process of claim 1 wherein said matrix comprises silica-alumina.
9. The process of claim 6 wherein colloidal dispersions of silica and alumina are used.
10. The process of claim 1 wherein the zeolite is ZSM-5.
11. The process of claim 2 wherein the zeolite is ZSM-5.
12. The process of claim 3 wherein the zeolite is ZSM-5.
13. The process of claim 4 wherein the zeolite is ZSM-5.
14. The process of claim 5 wherein the zeolite is ZSM-5.
15. The process of claim 13 wherein the catalyst has become partially inactivated as a result of syngas conversion and its activity is restored.
16. The process of claim 15 wherein step (a) is omitted.

* * * * *